United States Patent
Reinshagen et al.

(10) Patent No.: US 8,201,998 B2
(45) Date of Patent: Jun. 19, 2012

(54) METHOD FOR DETERMINING THE TEMPERATURE OF A MEASUREMENT SENSOR

(75) Inventors: Holger Reinshagen, Bamberg (DE); Lothar Diehl, Gerlingen (DE)

(73) Assignee: Robert Bosch GmbH, Stuttgart (DE)

( * ) Notice: Subject to any disclaimer, the term of this patent is extended or adjusted under 35 U.S.C. 154(b) by 705 days.

(21) Appl. No.: 12/374,362

(22) PCT Filed: Oct. 23, 2007

(86) PCT No.: PCT/EP2007/061322
§ 371 (c)(1),
(2), (4) Date: Jan. 19, 2009

(87) PCT Pub. No.: WO2008/058834
PCT Pub. Date: May 22, 2008

(65) Prior Publication Data
US 2009/0308135 A1     Dec. 17, 2009

(30) Foreign Application Priority Data
Nov. 15, 2006  (DE) .......... 10 2006 053 808

(51) Int. Cl.
*G01K 7/18*     (2006.01)
*G05D 23/24*    (2006.01)

(52) U.S. Cl. ........................................... 374/142
(58) Field of Classification Search ............ 374/142
See application file for complete search history.

(56) References Cited

U.S. PATENT DOCUMENTS

| | | | |
|---|---|---|---|
| 4,535,316 A * | 8/1985 | Wertheimer et al. | 338/34 |
| 4,875,981 A * | 10/1989 | Usami et al. | 205/785 |
| 4,900,412 A * | 2/1990 | Ker et al. | 204/427 |
| 5,562,811 A * | 10/1996 | Lenfers | 204/408 |
| 5,719,778 A * | 2/1998 | Suzumura et al. | 700/207 |
| 6,266,993 B1 * | 7/2001 | Diehl et al. | 73/1.06 |
| 6,367,309 B1 * | 4/2002 | Diehl et al. | 73/23.32 |
| 6,571,602 B2 * | 6/2003 | Ohkuma | 73/23.32 |
| 6,812,436 B2 | 11/2004 | Nomura et al. | |
| 7,036,982 B2 * | 5/2006 | Smith et al. | 374/144 |
| 7,316,767 B2 * | 1/2008 | Tanaka | 204/425 |
| 7,976,689 B2 * | 7/2011 | Scheffel et al. | 204/406 |
| 2004/0047396 A1 | 3/2004 | Nomura et al. | |

FOREIGN PATENT DOCUMENTS

| | | |
|---|---|---|
| DE | 41 06 308 | 9/1992 |
| DE | 198 38 456 | 3/2000 |
| EP | 0 695 983 | 2/1996 |
| JP | 2000-292407 | 10/2000 |

* cited by examiner

*Primary Examiner* — Christopher Fulton
(74) *Attorney, Agent, or Firm* — Merchant & Gould P.C

(57) ABSTRACT

A method for determining a temperature of a measurement sensor for determining an oxygen concentration in gas mixtures. In particular, the measurement sensor may be used in exhaust gases of internal combustion engines. A detection voltage which corresponds to the oxygen concentration and is provided by a Nernst measuring cell is evaluated, and the measurement sensor is regulated to an operating temperature using a heating device. The internal resistance of the Nernst measuring cell is determined in a first temperature range and is used to infer the temperature of the Nernst measuring cell, and the internal resistance of the heating device is determined in a second temperature range and is used to infer the temperature of the Nernst measuring cell.

10 Claims, 4 Drawing Sheets

METHOD FOR DETERMINING THE TEMPERATURE OF A MEASUREMENT SENSOR

TECHNICAL FIELD

The invention relates to a procedure for determining the temperature of a measurement sensor.

The invention also relates to a computer program and a computer program product with a program code, which is saved on a machine readable device, for implementing the procedure.

BACKGROUND

A procedure conforming to its genre for regulating the temperature of a measurement sensor for determining an oxygen concentration in gas mixtures, in particular exhaust gases of combustion engines, is known from DE 198 38 456 A1, at which a detection voltage that corresponds with the oxygen concentration and that is supplied by the Nernst measuring cell is evaluated, whereby the measurement sensor is regulated to an operating temperature by a heating device and the actual operating temperature is determined from a measurement of an alternating current internal resistance of the Nernst cell. In order to eliminate manufacturing related variations of the resistance value this procedure determines an alternating current internal resistance of a feed line of electrodes of the Nernst cell when starting and/or re-starting the measurement sensor and by considering the determined actual alternating current internal resistance when determining the operating temperature. The determination of the operating temperature of the measurement sensor due to the internal resistance of the Nernst cell is only possible in a limited range, because the temperature characteristic line of the resistance of the electrolyte that creates the measurement sensor allows only a precise measurement in a limited temperature range due to its course. Furthermore the characteristic line provides a varying offset due to the feed line resistance. The characteristic line is also having errors by typographic inaccuracies.

SUMMARY

The procedure according to the invention includes a method for determining the temperature of a measurement sensor for determining an oxygen concentration in gas mixtures. In particular, in exhaust gases of internal combustion engines, a detection voltage, which corresponds to the oxygen concentration and is provided by a Nernst measuring cell, is evaluated, and the measurement sensor is regulated to an operating temperature using a heating device. The method is characterized in that the internal resistance of the Nernst measuring cell is determined in a first temperature range and is used to infer the temperature of the Nernst measuring cell, and in that the internal resistance of the heating device is determined in a second temperature range and is used to infer the temperature of the Nernst measuring cell. The procedure has the advantage that a determination of the temperature of a measurement sensor for determining an oxygen concentration in gas mixtures is possible over a big temperature range with a high precision. According to the invention, it is therefore provided that the internal resistance of the Nernst cell is determined in a first temperature range, and from this the temperature of the Nernst cell is inferred, and in that in a second temperature range the internal resistance of the heating device is determined from which the temperature of the Nernst cell is inferred. By dividing the operating area of such a measurement sensor into several temperature ranges, which are chosen in such a way that a precise determination of the temperature of the Nernst cell is possible, an exact temperature determination is possible over the entire operating area of the measurement sensor.

Due to the measures of the present disclosure, many advantageous improvements and advancements of the procedure are possible.

Thus, the determination of the internal resistance of the heating device and the inferring of the temperature of the Nernst cell from this internal resistance preferably takes place in the second temperature range when the heating device is turned off. Thereby, for example, the cycle times can always be used at a cycled controlling of the heating device, in which the heating device is not impinged with a voltage/a current.

It is provided in an advantageous embodiment that the two temperature ranges do not overlap, but are separated from each other. Thereby the first temperature range preferably ends below the operating temperature of the measurement sensor, while the second temperature range starts above the operating temperature range of the measurement sensor. This has the advantage that in the first temperature range, thus at lower temperatures below the operating temperature, a very precise temperature determination is enabled by measuring the internal resistance of the Nernst cell. Thus, the temperature characteristic line of the electrolyte resistance provides a big ascent in this range and severely changes insofar with the temperature and therefore allows a high resolution. In the second temperature range, which begins above the operating temperature of the measurement sensor, the temperature of the measurement sensor is determined, on the other hand, by determining the internal resistance of the heating device. This is based on the idea that the characteristic line of the internal resistance of the heating device runs linear and also provides an ascent in the range of higher temperatures, which allows a sufficiently high resolution.

Another embodiment, on the other hand, provides that the temperature ranges overlap. In this case, the temperature of the Nernst cell is determined from the determination of the internal resistance of the Nernst cell and also from the determination of the internal resistance of the heating device. Thus, two measurements are undertaken with different measuring procedures in the same temperature range so that two temperature values result. The internal resistance of the Nernst cell is thereby preferably used, whose feed line part is compensated as it is already explained in the previously mentioned DE 198 38 456 A1. The second temperature value is used for a reasonability evaluation of this value.

In order to calibrate the temperature characteristic line of the internal resistance of the heating device regarding its absolute value, it is provided in one embodiment of the procedure that directly below the operating temperature of the measurement sensor not only the internal resistance of the Nernst cell but also the internal resistance of the heating device are determined and that by comparing the internal resistance of the Nernst cell with the resistance of the heating device the absolute value of the temperature characteristic line of the resistance of the heating device is calibrated. Thus, put in other words, the calibration takes place in a temperature range, in which a very precise temperature determination is possible by determining the internal resistance of the Nernst cell.

This calibration takes place when in a new condition, and it is saved and used over the operational life span of the measurement sensor. In so far as it is possible to compensate the error that is caused by the ageing of the internal resistance of the Nernst cell, since the internal resistance of the heating device is known here.

In the temperature range, in which the calibration is carried out, a separation of the offset-error and of a proportional error that falsifies the characteristic line can be furthermore undertaken for another optimization thereby that the relation of the meander resistance of the meander formed heating device to the feed line resistance can be inferred from a comparison of the internal resistance of the turned on heating device with the internal resistance of the turned off heating device. In doing so, the offset-error can be separated from the proportional error and also the proportional error of the linear characteristic line can be compensated since the offset-error is eliminated by the calibration.

BRIEF DESCRIPTION OF THE DRAWINGS

Embodiments of the invention are illustrated in the following drawings and explained in the subsequent description.

It is shown in.

DETAILED DESCRIPTION

Figure 1:
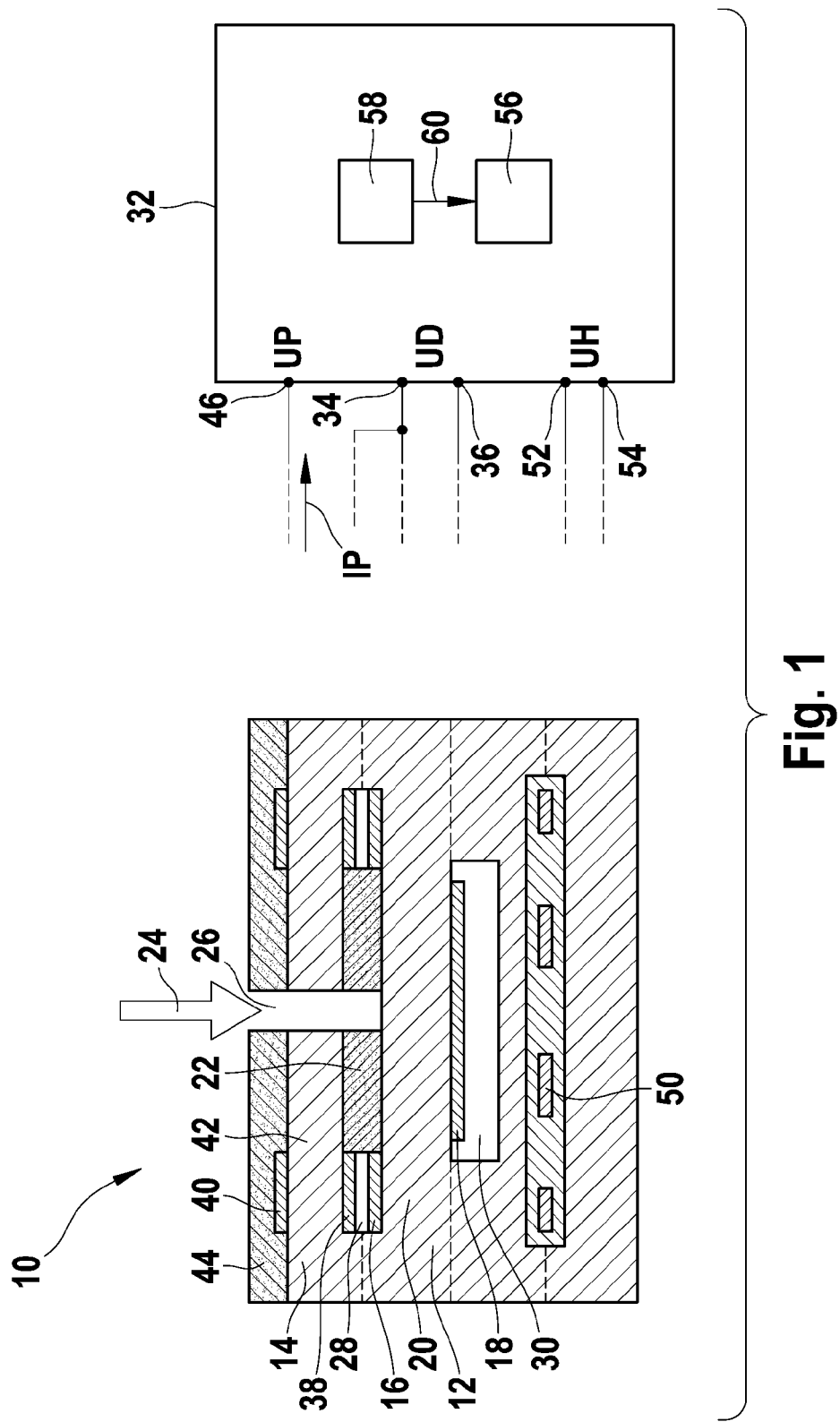
FIG. 1 is a cross-sectional view through a measurement sensor, which uses the procedure according to the invention.

FIG. 1 shows measurement sensor 10 in a cross-sectional view through a measuring head. The measurement sensor 10 is arranged as planar wide-band measurement sensor and consists of a number of individual layers that are arranged on top of each other, which, for example, can be structured by tape casting, blanking, silk-screening, laminating, cutting, sintering and such alike. It shall not be further deferred to the attainment of the layer creation in the scope of the present description, since it is known.

The measurement sensor 10 serves for determining an oxygen concentration in exhaust gases of combustion engines, in order to get a control signal for adjusting a fuel-air mixture, with which the combustion engine is operated. The measurement sensor 10 has a Nernst cell 12 and a pump cell 14. The Nernst cell 12 has a first electrode 16 and a second electrode 18, in between which a solid electrolyte 20 is arranged. The electrode 16 is exposed to the exhaust gas 24 that has to be measured over a diffusion barrier 22.

The measurement sensor 10 has a measuring opening 26, which can be impinged with the exhaust gas 24. The diffusion barrier 22 spreads at the bottom of the measurement opening 26, whereby it comes to the creation of a cavity 28, within which the electrode 16 is arranged. The electrode 16 of the Nernst cell 12 is arranged in a reference air channel 30 and is exposed to a reference gas that is in the reference channel 30, for example air. The solid electrolyte 20 consist, for example, of yttrium oxide stabilized zirconium oxide, while the electrodes 16 and 18 consist of, for example, platinum and zirconium oxide.

The measurement sensor 10 is connected with an indicated circuit arrangement 32, which serves for the evaluation of signals of the measurement sensor 10 and for controlling the measurement sensor 10. The electrodes 16 and 18 are hereby connected with inlets 34 or 36, at which a detection voltage UD of the Nernst cell is applied.

The pump cell 14 consists of a first electrode 38 and a second electrode 40, in between which a solid electrolyte 42 is arranged. The solid electrolyte 42 consists again of, for example, an yttrium oxide stabilized zirconium oxide, while the electrodes 38 and 40 again can consist of platinum and zirconium oxide. The electrode 38 is also arranged in the cavity 28 and therefore is also exposed to the exhaust gas 24 over the diffusion barrier 22. The electrode 40 is covered with a protective layer 44, which is porous, so that the electrode 40 is directly exposed to the exhaust gas 24. The electrode 40 is connected with the inlet 46 of the circuit arrangement 32, while the electrode 38 is connected with the electrode 16 and lies together with it at the inlet 34 of the circuit arrangement 32.

The measurement sensor 10 comprises furthermore a heating device 50, which is build by a so-called heating meander and connected with the inlets 52 and 54 of the circuit arrangement 32. At the inlets 52 and 54 a heating voltage UH can be applied by a regulating circuit.

The function of the measurement sensor follows:

The exhaust gas 24 abuts over the measurement opening 26 and the diffusion barrier 22 in the cavity 28 and thus at the electrodes 16 of the Nernst cell 12 and the electrode 38 of the pump cell 14. Due to the present oxygen concentration in the exhaust gas 24 that has to be measured, an oxygen concentration difference occurs between the electrode 16 and the electrode 18 that is exposed to the reference gas. By the connection 34 the electrode 16 is connected with a current source of the circuit arrangement 32, which delivers a constant current. Due to the present oxygen concentration difference at the electrodes 16 and 18, a certain detection voltage (Nernst voltage) UD occurs. The Nernst cell 12 works hereby as a lambda probe which detects whether a high or a low oxygen concentration is present in the exhaust gas 24. Due to the oxygen concentration, it is clear whether the fuel-air mixture, with which the combustion engine is operated, is a rich or a lean mixture. At a change from a rich to a lean range, the detection voltage UD decreases or increases vice versa.

With the aid of the circuit arrangement 32, the detection voltage UD is used for detecting a pump voltage UP with which the pump cell 14 is impinged between its electrodes 38 or 40. Depending on whether it is signalized by the detection voltage UD that the air-fuel mixture is in a rich or lean range, the pump voltage UP is negative or positive, so that the electrode 40 is either a cathode or an anode. Correspondingly a pump current IP sets in, which can be measured by a measuring device of the circuit arrangement 32. With the aid of the pump current IP, oxygen ions are either pumped from the electrode 40 to electrode 38 or reversely. The measured pump current IP serves for controlling a device for adjusting the air-fuel mixture, with which the combustion engine is operated.

The heating voltage UH can be applied at the outlets 54 and 52 of the circuit arrangement 32 over the regulating device 56 so that the heating device 50 can be turned on or off. Due to the heating device 50, the measurement sensor 10 can be brought to an operating temperature of over approximately 780° C. Due to the speed variations of the exhaust gas 24, the measurement sensor 10 is impinged over the exhaust gas 24 with a specific varying heat energy. Depending on the heating of the measurement sensor 10 over the exhaust gas 24, an activation or deactivation of the heating device 50 is necessary. In order to determine the actual operating temperature of the measurement sensor 10, the circuit arrangement 32 has a measure arrangement 58 with which an alternating current internal resistance of the Nernst cell 12, including its feed line to the circuit arrangement 32, can be measured. The alternating current internal resistance of the Nernst cell 12 depends on temperature so that the operating temperature can be inferred from the measured alternating current internal resistance of the Nernst cell 12. Depending on the determined operating temperature, the measure arrangement 58 provides a signal 60 to the heating control 56.

The detection of the alternating current internal resistance of the Nernst cell 12 is basically known and emerges, for example, from DE 198 38 456, column 4, line 57, to column 6, line 10, which is hereby incorporated by reference in its entirety. The measurement by an electrolyte resistance $R_I$ of the Nernst cell 12 takes place by taking advantage of the NTC-effect.

Due to the measurement of the resistance, the temperature is determined and the heat output correspondingly regulated so that the probe is adjust to the operating temperature. As long as the probe is not heated internally but only by the exhaust gas, the ambient or exhaust gas temperature can be determined by the resistance measurement. But this measurement is only possible in a limited temperature range up to ca. 800° C. A measurement above this temperature is not possible without further ado.

Figure 2A:
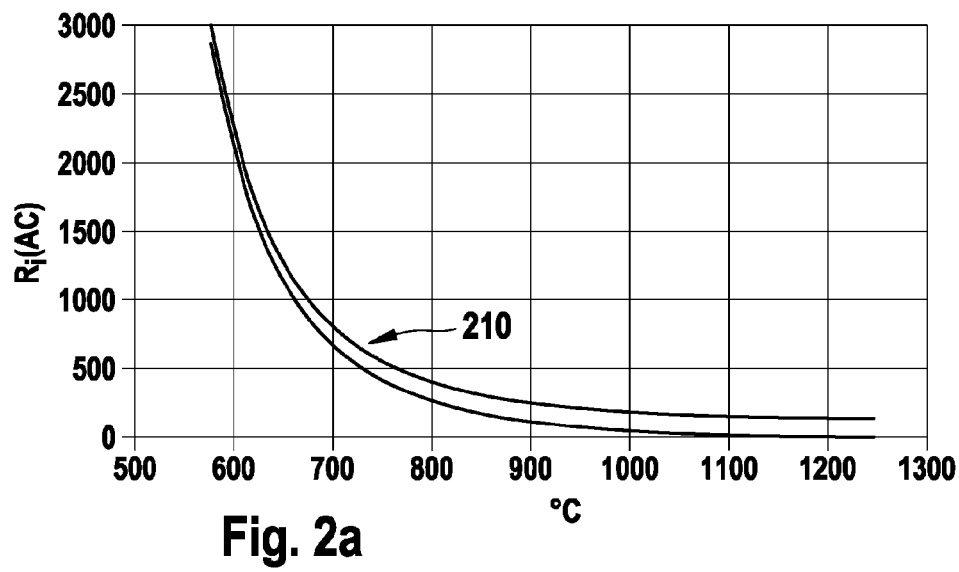
FIG. 2a shows schematically an internal resistance of the Nernst cell over the temperature range.

Within the scope of the determinations of the ambient or exhaust gas temperature, especially high temperatures over 800° C., are now of interest. Due to the exponential drop, the resistance characteristic line over the temperature runs flat in this temperature range, as is shown in FIG. 2a, where the characteristic line of the internal resistance of the Nernst cell 12 is registered over the temperature. Moreover, the tolerance of the characteristic line 210 experiences a widening, because the relative part of the manufacturing related scattering feed line that only slightly depends on temperature resistance increases. Therefore, the determination of higher temperatures based on the electrolyte resistance of the Nernst cell 12 or also of the pump cell is afflicted with a significant error.

Figure 2B:
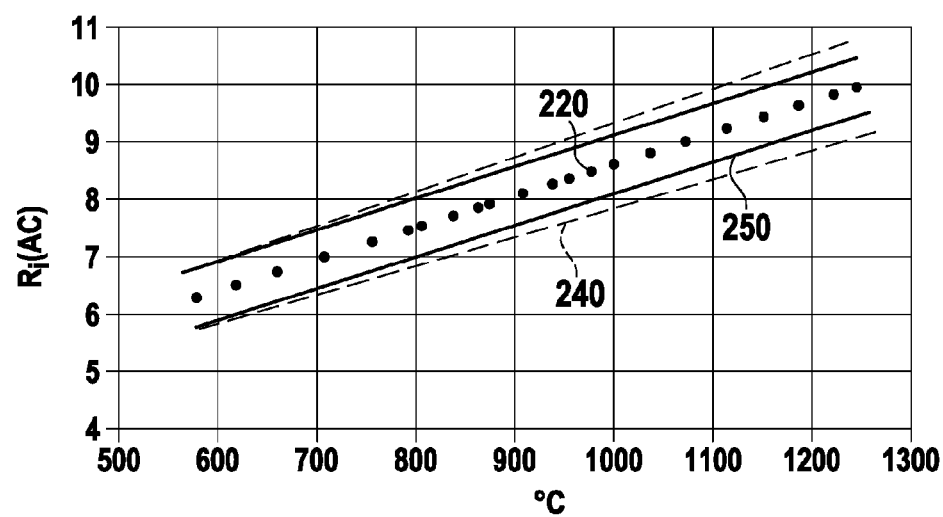
FIG. 2b shows schematically the internal resistance of the heating device over the temperature range.
Figure 3:
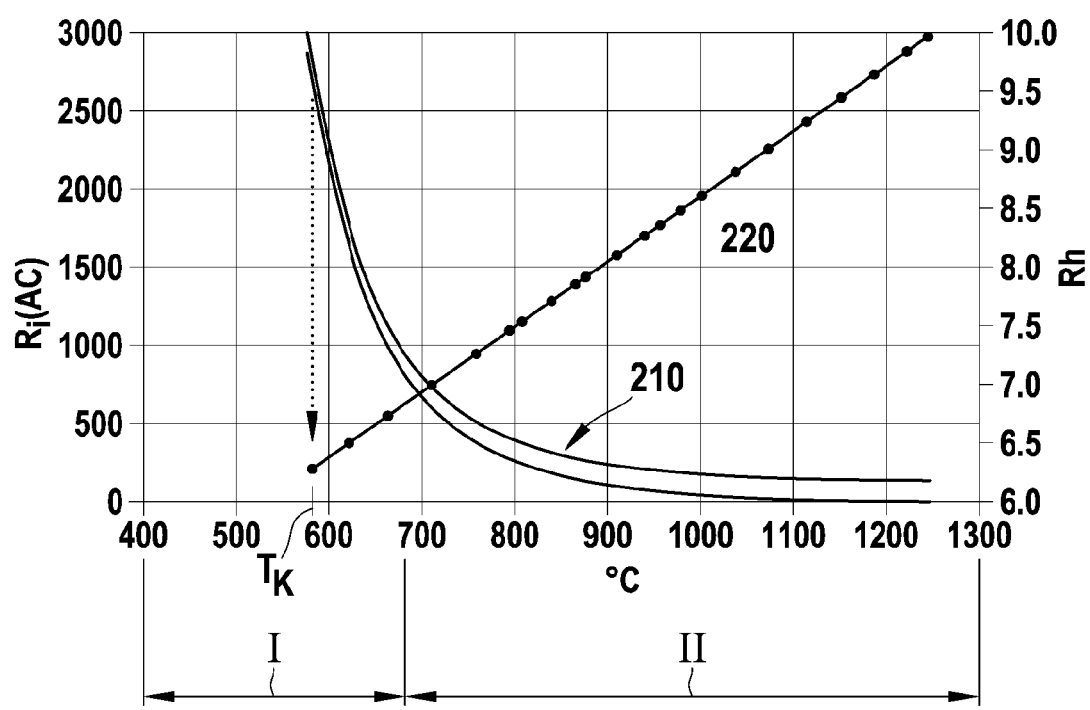
FIG. 3 shows schematically the procedure according to the invention for regulating the temperature of a measurement sensor by temperature characteristic lines of the resistance of the Nernst cell as well as the internal resistance of the heating device that are shown in a diagram.

In contrast to the internal resistance of the Nernst cell 12, thus to the resistance of the electrolyte, the metallic resistance of the heating device 50 shows a steeper increase with the temperature that is linear and in the higher temperature range that is bigger than 800° C., as shown in FIG. 2b. Nevertheless, the internal resistances of the heating device 50 are approximately lower by one scale than the internal resistances of the Nernst cell 12, so that an unknown offset, for example by a feed line resistance, causes an increased error of the correlation of internal resistances of the heating device 50 and ambient or exhaust gas temperature. In order to be able to operate such a measurement sensor 10 in a big temperature range of approximately 500° C. to 1200° C. with a high precision, it is now provided to undertake a determination of the temperature in a first temperature range by the internal resistance Ri of the Nernst cell 12 and a determination of the temperature in a second temperature range based on the internal resistance Ri of the heating device 50, as it is schematically shown in FIG. 3. In a first temperature range that is labeled with I, in which the internal resistance Ri of the Nernst cell 12 over the temperature shows a steep drop, the temperature of the measurement sensor I is determined by determining the internal resistance. In a second temperature range, labeled with II, in which the internal resistance of the Nernst cell 12 over the temperature changes only slightly, the ascertainment of the temperature of the measurement sensor takes place by determining the internal resistance of the heating device 50.

It can also be provided to carry out a determination of the temperature of the internal resistance of the heating device 50 in the range labeled with I, and to compare the temperature value that has been determined this way with the temperature value, which has been determined by determining the internal resistance of the Nernst cell 12. The average value of those two temperatures that have been determined this way can be thereby also calculated. The same applies to the range labeled with II. The procedure also allows the determination of the offset of the feed line resistance, which required additional, not uncomplicated measuring methods according to the state of the art, and to calibrate the temperature characteristic line of the internal resistance of the heater 50 during running operation or during the starting phase. By this calibration, that is further explained hereinafter, the measurement of the internal resistance of the heater 50 can take place with an increased accuracy. This provides the following advantages:

no erroneous temperature characteristic line of the internal resistance of the heater 50 due to typographically varying resistances of the heating device 50;

unknown offsets of the temperature characteristic line of the heater 50 due to the varying feed line resistance are eliminated; and additional temperature sensors can be waived.

The calibration of the temperature characteristic line of the internal resistance of the heating device 50 takes place in such a way that a precise temperature determination is carried out at a temperature $T_k$ due to the temperature characteristic line 210 of the internal resistance of the Nernst cell 12. Based on this measurement or several such measurements the characteristic line of the internal resistance of the heating device 50 is now calibrated regarding its absolute value. At higher temperatures in the range II the determination of the temperature takes place now with the aid of the calibrated temperature characteristic line of the internal resistance of the heating device 50.

The above explained that temperature measurement takes place when the heating device is switched off. At a cycled controllable heater it takes place always in the time interval, in which the heater is not impinged with a current/voltage.

Figure 4:
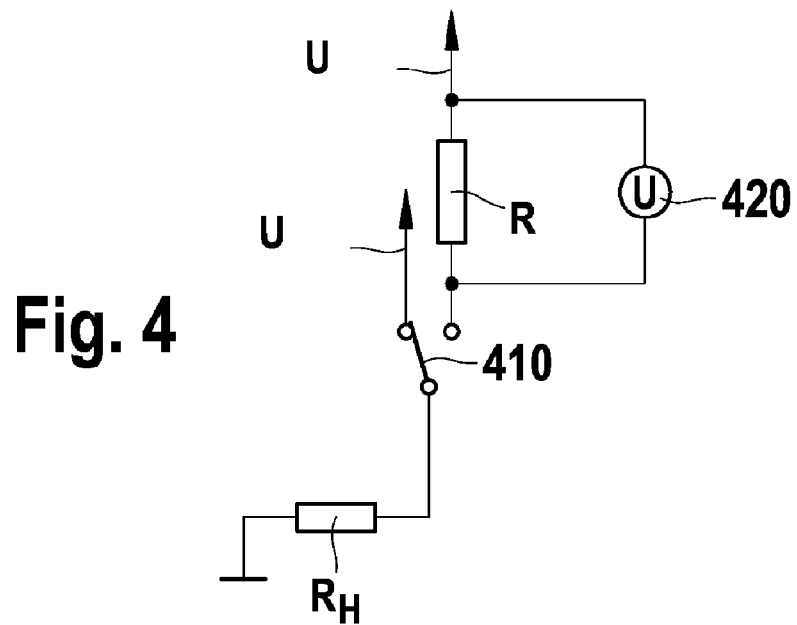
FIG. 4 shows schematically a circuit for detecting the internal resistance of the heating device.

The detection can, for example, take place when—as shown in FIG. 4—the heating device is not impinged with the battery voltage $U_{Bat}$, but is connected, for example, by an electronic switch 410 with a measuring arrangement, which comprises a shunt resistance $R_{shunt}$, at which the voltage drop that drops above it is measured by a volt meter 420 and thus the internal resistance is determined. The shunt resistance $R_{shunt}$ can thereby, for example, provide a value of 3 ohm, which allows a very precise resistance determination, since no drop that has been caused by the resistance reduces the power of the heating device in the case of the switched-off heater, also at a higher shunt resistance $R_{shunt}$.

By a comparison of the internal resistance of the heating device 50 at two very different temperatures of the measurement sensor 10, the relation of the meander resistance to the feed line resistance can be inferred. This way an error 240 that is associated with the heating meander can be distinguished from an error 250 that is associated with the feed lines (compare FIG. 2b). In particular, the resistance of the heater is built by the feed line and meander resistance, whereby the meander resistance is depending on the temperature. If now the resistance is measured at two temperatures, for example directly after starting the motor vehicle and after a time, during which the operating temperature of the sensor of 780° C. is already achieved, the resistance variation of the heating device 50 and from that of the meander resistance, which is proportional to the resistance variation, can be determined. The part of the feed lines can be determined with the meander resistance from the resistance of the heating device 50. An offset error can be thereby distinguished from a proportional error.

A compensation of the offset error and the proportional error can also take place due to two or more measuring points at two or more temperatures. The condition for that is the above described calibration of the characteristic line 220 at a point $T_k$ due to the exact temperature determination by the temperature characteristic line 210 of the internal resistance of the Nernst cell 12.

Figure 5:
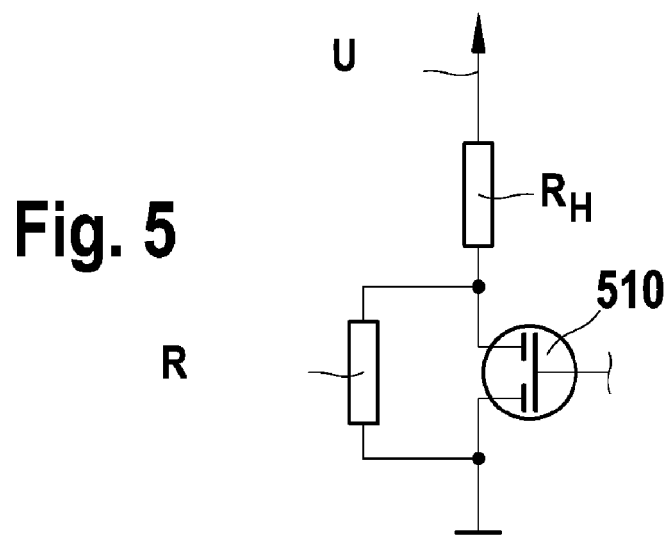
FIG. 5 shows schematically another circuit for detecting the internal resistance of the heating device.

A measurement of the internal resistance Rx of the heating device 50 can furthermore take place by a circuit over a shunt, which is applied parallel to a currentless outlet of a field effect transistor 510, as is schematically shown in FIG. 5. This shunt $R_{shunt}$ provides, in this case, a value of, for example, one kilo ohm. In this case no changeover between switched-on and switched-off heater has to be carried out.

The method described herein can, for example, be implemented as and run in a computer program on a computer, in particular a control unit of a combustion engine. The program code can be saved on a machine readable device, which can be read by the control unit.

The invention claimed is:

1. A method of determining a temperature of a measurement sensor that determines an oxygen concentration in an exhaust gas of an internal combustion engine, wherein a detection voltage that corresponds to the oxygen concentration is evaluated, and wherein the detection voltage is provided by a Nernst measuring cell, the method comprising:
    regulating the measurement sensor to an operating temperature using a heating device;
    determining an internal resistance of the Nernst measuring cell in a first temperature range to infer the temperature of the Nernst measuring cell; and
    determining an internal resistance of the heating device in a second temperature range to infer the temperature of the Nernst measuring cell.

2. The method of claim 1, further comprising determining the internal resistance of the heating device when the heating device is turned off.

3. The method of claim 1, wherein the first temperature range and the second temperature range do not overlap.

4. The method of claim 3, wherein the first temperature range ends below the operating temperature of the measurement sensor, and wherein the second temperature range starts above the operating temperature of the measurement sensor.

5. The method of claim 1, wherein the first temperature range and the second temperature range overlap.

6. The method of claim 5, further comprising simultaneously determining:
    the internal resistance of the Nernst measuring cell in the first and second temperature range, wherein a first temperature of the Nernst measuring cell can be inferred from said determination; and
    the internal resistance of the heating device, wherein a second temperature of the Nernst measuring cell can be inferred from said determination;
    wherein the temperature of the measurement sensor is inferred from the first and second temperatures.

7. The method of claim 1, further comprising:
    determining the internal resistance of the Nernst measuring cell and the internal resistance of the heating device in a default temperature range preferably below the operating temperature of the measurement sensor; and
    performing an absolute value calibration by calibrating an absolute value of a temperature characteristic line of the internal resistance of the heating device by a comparison of the internal resistance of the Nernst measuring cell with the internal resistance of the heating device.

8. The method of claim 7, further comprising:
    performing the absolute value calibration a single time in a new condition; and saving and using the absolute value calibration over an operational life span of the measurement sensor.

9. A computer program to implement, if executed on a computer, all steps of a method of determining a temperature of a measurement sensor that determines an oxygen concentration in an exhaust gas of an internal combustion engine, wherein a detection voltage that corresponds to the oxygen concentration is evaluated, and wherein the detection voltage is provided by a Nernst measuring cell, the method comprising: regulating the measurement sensor to an operating temperature using a heating device; determining an internal resistance of the Nernst measuring cell in a first temperature range to infer the temperature of the Nernst measuring cell; and determining an internal resistance of the heating device in a second temperature range to infer the temperature of the Nernst measuring cell.

10. A computer program product with a program code saved on a machine readable device to implement, if executed on a computer or a control unit, a method of determining a temperature of a measurement sensor for determining an oxygen concentration in an exhaust gas of an internal combustion engine, wherein a detection voltage that corresponds to the oxygen concentration is evaluated, and wherein the detection voltage is provided by a Nernst measuring cell, the method comprising: regulating the measurement sensor to an operating temperature using a heating device; determining an internal resistance of the Nernst measuring cell in a first temperature range to infer the temperature of the Nernst measuring cell; and determining an internal resistance of the heating device in a second temperature range to infer the temperature of the Nernst measuring cell.

\* \* \* \* \*